(12) United States Patent
Jinnoh et al.

(10) Patent No.: US 11,662,161 B2
(45) Date of Patent: May 30, 2023

(54) HEAT CONDUCTION DEVICE

(71) Applicant: DENSO CORPORATION, Kariya (JP)

(72) Inventors: Masanori Jinnoh, Kariya (JP); Aun Ota, Kariya (JP); Hisayoshi Oshima, Kariya (JP); Hidehiko Hiramatsu, Kariya (JP); Takashi Kaneko, Kariya (JP)

(73) Assignee: DENSO CORPORATION, Kariya (JP)

( * ) Notice: Subject to any disclaimer, the term of this patent is extended or adjusted under 35 U.S.C. 154(b) by 486 days.

(21) Appl. No.: 16/438,630

(22) Filed: Jun. 12, 2019

(65) Prior Publication Data
US 2019/0331437 A1 Oct. 31, 2019

Related U.S. Application Data

(63) Continuation of application No. PCT/JP2017/042492, filed on Nov. 28, 2017.

(30) Foreign Application Priority Data

Dec. 19, 2016 (JP) .............................. JP2016-245478
Sep. 27, 2017 (JP) .............................. JP2017-186657

(51) Int. Cl.
*F28F 13/00* (2006.01)
*F28F 13/14* (2006.01)

(52) U.S. Cl.
CPC .............. *F28F 13/00* (2013.01); *F28F 13/14* (2013.01); *F28F 2013/001* (2013.01); *F28F 2013/006* (2013.01); *F28F 2013/008* (2013.01)

(58) Field of Classification Search
CPC ................. F28F 13/00; F28F 2013/001; F28F 2013/005; F28F 2013/006; F28F 2013/008; F28F 13/14; F28F 21/02; F28F 2265/10
See application file for complete search history.

(56) References Cited

U.S. PATENT DOCUMENTS 4,849,858 A * 7/1989 Grapes ................... H05K 1/056
                                                                    165/905
5,111,359 A * 5/1992 Montesano ............. F28F 21/00
                                                                    165/185

(Continued)

FOREIGN PATENT DOCUMENTS

CA         2 638 238 A1    1/2010
JP         S55-180188 U   12/1980
(Continued)

*Primary Examiner* — Jianying C Atkisson
*Assistant Examiner* — For K Ling
(74) *Attorney, Agent, or Firm* — Posz Law Group, PLC

(57) ABSTRACT

A heat conduction device includes a heat source portion, a temperature control surface, and heat transfer portions. The heat source portion is configured to generate at least hot heat or cold heat. The temperature control surface is sectioned into a plurality of temperature control sections, and at least some of the plurality of temperature control sections are disposed away from the heat source portion. The plurality of heat transfer portions connect the heat source portion and the plurality of the temperature control sections to transfer heat between the heat source portion and the plurality of temperature control sections. The plurality of temperature control sections are separated from each other based on a distance from the heat source portion.

22 Claims, 13 Drawing Sheets

(56) References Cited

U.S. PATENT DOCUMENTS

| | | | | |
|---|---|---|---|---|
| 5,224,030 | A | * | 6/1993 | Banks .................... F28F 21/02 165/185 |
| 5,287,248 | A | * | 2/1994 | Montesano ............. F28F 21/00 165/185 |
| 5,316,080 | A | * | 5/1994 | Banks .................... F28F 21/02 165/185 |
| 5,390,734 | A | * | 2/1995 | Voorhes ................. F28F 13/00 257/E23.105 |
| 5,769,158 | A | * | 6/1998 | Yao ........................ F28F 13/00 165/185 |
| 6,027,807 | A | | 2/2000 | Inoue et al. |
| 6,037,066 | A | * | 3/2000 | Kuwabara ............... B22F 7/008 257/675 |
| 6,060,166 | A | * | 5/2000 | Hoover ................. B29C 70/546 428/408 |
| 6,501,647 | B1 | * | 12/2002 | Cepeda .................... G06F 1/20 257/E23.083 |
| 7,319,590 | B1 | * | 1/2008 | Ingram ................ H01L 23/367 257/713 |
| 10,299,407 | B2 | * | 5/2019 | Hurbi ................... H01L 23/373 |
| 2002/0059905 | A1 | * | 5/2002 | Gorokhovsky ....... C23C 16/458 118/724 |
| 2005/0145369 | A1 | * | 7/2005 | Huang ................ F28D 15/0275 165/104.11 |
| 2009/0101306 | A1 | | 4/2009 | Reis et al. |
| 2011/0198067 | A1 | * | 8/2011 | Hada ................... H05K 7/20454 165/185 |
| 2011/0303399 | A1 | * | 12/2011 | Sakimichi ............... H01L 23/36 165/185 |
| 2014/0363718 | A1 | * | 12/2014 | Andres ............ H01M 10/6554 429/120 |
| 2014/0367074 | A1 | * | 12/2014 | Hirasawa ........... F28D 15/0275 165/104.26 |
| 2015/0075762 | A1 | * | 3/2015 | Narendra ................ F28F 21/02 165/185 |
| 2016/0017603 | A1 | | 1/2016 | Cha |
| 2018/0023904 | A1 | * | 1/2018 | Kato ....................... B32B 27/36 165/80.2 |

FOREIGN PATENT DOCUMENTS

| | | |
|---|---|---|
| JP | H10-131390 A | 5/1998 |
| JP | 2004-050888 A | 2/2004 |
| JP | 2010-038470 A | 2/2010 |
| JP | 2012-096560 A | 5/2012 |
| JP | 2013-019645 A | 1/2013 |
| JP | 2014-240269 A | 12/2014 |
| JP | 2015-092101 A | 5/2015 |

* cited by examiner

HEAT CONDUCTION DEVICE

CROSS REFERENCE TO RELATED APPLICATION

The present application is a continuation application of International Patent Application No. PCT/JP2017/042492 filed on Nov. 28, 2017, which designated the U.S. and claims the benefit of priority from Japanese Patent Application No. 2016-245478 filed on Dec. 19, 2016, and Japanese Patent Application No. 2017-186657 filed on Sep. 27, 2017. The entire disclosures of all of the above applications are incorporated herein by reference.

TECHNICAL FIELD

The present disclosure relates to a heat conduction device that transfers heat of a heat source.

BACKGROUND

A heat conduction device is known, which takes heat of a human body or supplies heat to the human body by heat conduction by using, as a heat source (hot heat source or cold heat source), a peltier device or a metal pipe through which a heat medium whose temperature is controlled.

SUMMARY

A heat conduction device according to an aspect of the present disclosure includes a heat source portion, a temperature control surface, and a heat transfer portion. The heat source portion generates at least hot heat or cold heat. The temperature control surface is sectioned into multiple temperature control sections, and at least some of the multiple temperature control sections are distance away from the heat source portion. The heat transfer portions connect the heat source portion and the temperature control sections so as to transfer heat therebetween.

EMBODIMENTS

Figure 1:
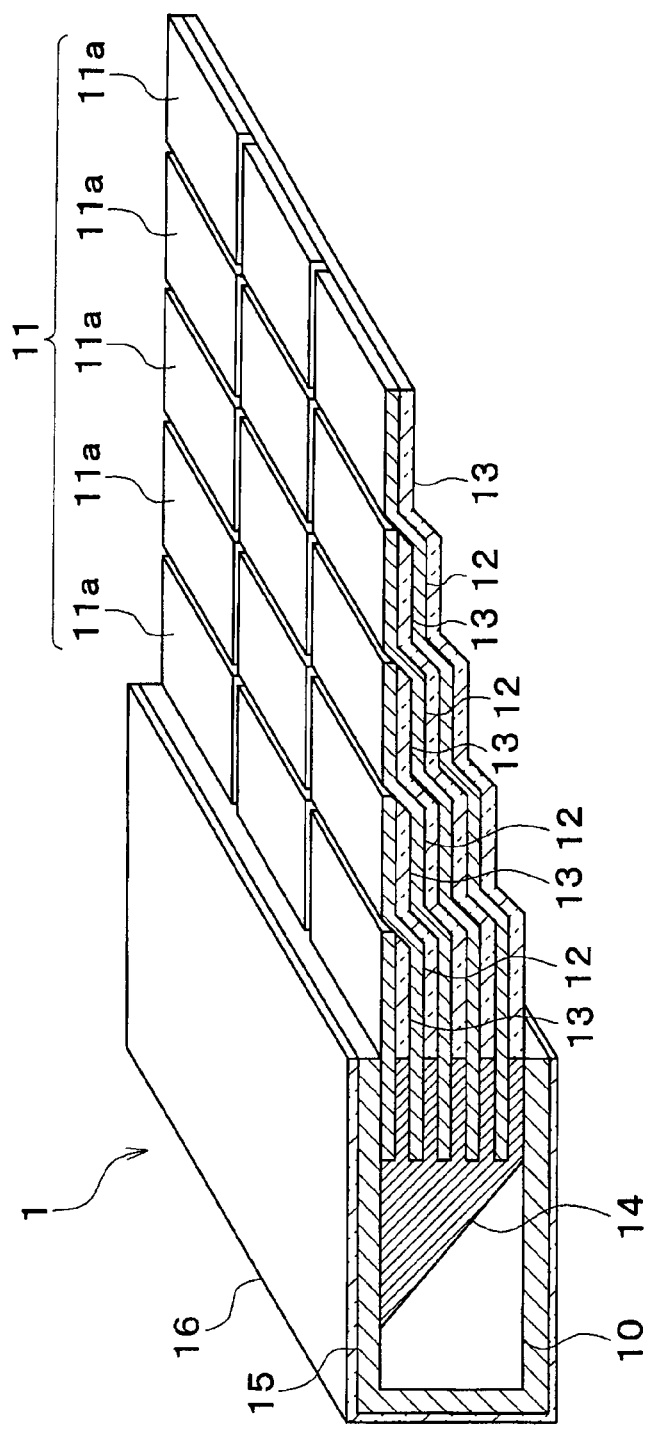
FIG. 1 is a perspective view illustrating a heat conduction device according to at least one embodiment of the present disclosure.

Hereinafter, embodiments for implementing the present disclosure will be described referring to drawings. In each embodiment, portions corresponding to the elements described in the preceding embodiments are denoted by the same reference numerals, and redundant explanation may be omitted. In each of the embodiments, when only a part of the configuration is described, the other parts of the configuration can be applied to the other embodiments described above. The present disclosure is not limited to combinations of embodiments which combine parts that are explicitly described as being combinable. As long as no problems are present, the various embodiments may be partially combined with each other even if not explicitly described.

First Embodiment

A first embodiment of the present disclosure will be described below with reference to the drawings. A heat conduction device 1 of the present embodiment is a cooling-heating device having a panel shape and can be used in a temperature control sheet for a vehicle, for example.

As shown in FIG. 1, the heat conduction device 1 of the present embodiment includes a heat source portion 10. The heat source portion 10 functions as a hot heat source supplying hot heat or a cold heat source supplying cold heat.

The heat source portion 10 of the present embodiment is a cooling water passage through which cooling water whose temperature is adjusted flows. In an example shown in FIG. 1, the cooling water flows inside the heat source portion 10 in a direction perpendicular to the drawing sheet.

The cooling water is a heat medium receiving hot heat of a heat generating device (not shown) or cold heat of a cooling device (not shown). The heat generating device is a device generating hot heat during its operation such as an internal combustion engine, a cooling water intercooler, and an inverter. The cooling device is a device generating cold heat during its operation such as a chiller of a refrigeration cycle.

The heat conduction device 1 includes a temperature control surface 11. At least a part of the temperature control surface 11 is distance away from the heat source portion 10. The temperature control surface 11 is a contact surface that contacts with a human body.

The temperature control surface 11 is sectioned into multiple temperature control sections 11a, and each of the temperature control sections is thermally connected with the heat source portion 10 by a heat transfer sheet 12 through a thermal resistance adjuster 14. One end of the heat transfer sheet 12 is connected to the above-described temperature control section 11a. The heat transfer sheet 12 corresponds to a heat transfer portion of the present disclosure. Since each of the temperature control sections 11a is connected to the heat source portion 10, each of the temperature control sections 11a can directly transfer heat of the heat source portion 10, and accordingly the temperature can be uniformed. Since the temperature control sections 11a are separated from each other based on a distance from the heat source portion 10, uniform temperature control can be performed. The uniform temperature control means adjusting to a temperature at which the user can feel warm or cold without feeling discomfort when the human body is in contact. The uniform temperature control provides a temperature distribution on the temperature control surface 11 in which a temperature difference between sections having high temperature and sections having low temperature is at or below 20 degrees Celsius, more preferably 10 degrees Celsius or 5 degrees Celsius, and accordingly the user can feel comfortable without feeling unpleasant.

In the present embodiment, the heat transfer sheet 12 and the temperature control sections 11a are integrated with each other, and a part of the heat transfer sheet 12 is the temperature control sections 11a. Accordingly, the heat transfer sheet 12 and the temperature control sections 11a are made of the same material. However, the material of the heat transfer sheet 12 may be different from that of the temperature control sections 11a. The temperature control surface 11 may be covered with fabric to improve comfort when the human body contacts as long as the human body senses warm and cold sufficiently when the heat is exchanged between the temperature control surface 11 and the human body. The surface of the temperature control surface 11 may be covered with a sheet member for protection.

Since the temperature control sections 11a are separated from each other based on a distance from the heat source portion 10, uniform temperature control can be performed. In an example shown in FIG. 1, the temperature control sections 11a are sectioned into five sections based on a distance from the heat source portion 10 (that is, in a left-right direction). The heat transfer sheets 12 are provided so as to correspond to the temperature control sections 11a sectioned based on the distance from the heat source portion 10. Since the heat transfer sheet 12 corresponding to the temperature control sections 11a farther from the heat source portion 10 is longer, the thermal resistance caused by the heat transfer sheet 12 is larger, and accordingly the heat from the heat source portion 10 is less likely to be transferred to the temperature control section 11a. Since the temperature control sections 11a are sectioned based on the distance from the heat source portion 10, the heat transfer from the heat source portion 10 to close temperature control sections 11a, to which the heat is easily transferred, and the heat transfer from the heat source portion 10 to distant temperature control sections 11a, to which the heat is hard to be transferred, can be adjusted, and accordingly uniform temperature control can be performed over the entire part of the temperature control surface 11. In the example shown in FIG. 1, the temperature control sections 11a separated from each other based on the distance from the heat source portion 10 are further sectioned into three sections along a direction perpendicular to a direction along which the temperature control surface 11 is sectioned based on the distance from the heat source portion 10. However, the temperature control sections 11a are not necessarily sectioned in the direction perpendicular to the direction along which the temperature control surface 11 is sectioned based on the distance from the heat source portion 10.

The lengths of the heat transfer sheets 12 are different from each other based on the distance between the temperature control section 11a and the heat source portion 10. In the example shown in FIG. 1, the heat transfer sheet 12 located on the upper side is short, and the heat transfer sheet 12 located on the lower side is long. If each of the temperature control sections 11a are made of the same material having the same properties, the same width, and the same thickness, the thermal resistance between the heat source portion 10 and the temperature control sections 11a varies based on the length of the heat transfer sheet 12. The uniform temperature control can be performed in the entire part of the temperature control surface 11 by adjusting the difference in the thermal resistance caused by the heat transfer sheet 12 to uniform the thermal resistance between the temperature control sections 11a and the heat source portion 10.

In the present embodiment, a thermal resistance adjuster 14 is provided between the heat source portion 10 and the heat transfer sheet 12 to adjust the difference of the thermal resistance caused by the difference of the lengths of the heat transfer sheets 12. The thermal resistance adjuster 14 is configured to adjust the thermal resistance between the heat source portion 10 and the temperature control sections 11a.

The thermal resistance adjuster 14 adjusts the thermal resistance between the heat source portion 10 and the temperature control sections 11a based on the distance between the heat source portion 10 and the temperature control section 11a, i.e. based on the length of the heat transfer sheet 12. The longer the heat transfer sheet 12 is, the larger the thermal resistance caused by the heat transfer sheet 12 is. The shorter the heat transfer sheet 12 is, the smaller the thermal resistance caused by the heat transfer sheet 12 is. The thermal resistance adjuster 14 adjusts the thermal resistance between the heat source portion 10 and the temperature control sections 11a connected by the short heat transfer sheet 12 to be large while the thermal resistance between the heat source portion 10 and the temperature control sections 11a connected by the long heat transfer sheet 12 does not increase. Specifically, the thermal resistance between the heat source portion 10 and the heat transfer sheet 12 can be adjusted by changing the length of the thermal resistance adjuster 14 between the heat source portion 10 and the heat transfer sheet 12. Here, as the heat transfer sheet 12 is longer, the length of the thermal resistance adjuster 14 in the left-right direction between the heat transfer sheet 12 and the heat source portion 10 is shortened. As the heat transfer sheet 12 is shorter, the length of the thermal resistance adjuster 14 in the left-right direction between the heat transfer sheet 12 and the heat source portion 10 is elongated.

Thereby, the thermal resistance between the heat source portion 10 and each temperature control section 11a can be uniformed, and the temperature distribution generated on the temperature control surface 11 can be uniformed.

In the present embodiment, the thermal resistance adjuster 14 is provided between the heat source portion 10 and the heat transfer sheet 12. However, the thermal resistance adjuster 14 may be provided inside the heat transfer sheet 12 or in the temperature control section 11a that is a contact part contacting with the human body.

The thermal resistance between the heat source portion 10 and the temperature control section 11a can be adjusted finely by using the thermal resistance adjuster 14 made of a low-thermal resistance material. If the thermal resistance is adjusted by the member having high thermal resistance, the thermal resistance is likely to be large even if the size of the member is small, and accordingly processing with very high dimensional accuracy is required. In contrast, when the member having low thermal resistance is used, it is possible to use the member having a large size when correcting the same amount of thermal resistance, and it is possible to reduce the required processing accuracy. Examples of the member having low thermal resistance include materials having high thermal conductivity such as graphite and various metal materials such as aluminum, copper, silver, gold, and titanium. When titanium is used, corrosion resistance can be improved. In contrast, materials having low thermal conductivity such as resin can be used as the member having low thermal resistance as long as the dimensions such as thickness of the material can be controlled with high accuracy, such as a film and a tape. In this case, it is also possible to give the heat resistance adjusting portion 14a function as a bonding member by using one having adhesiveness or stickiness.

As a method of adjusting the thermal resistance between the heat source portion 10 and each temperature control section 11a, not only the method providing the above-described thermal resistance adjuster 14 but also a method adjusting the thickness, shape, and thermal conductivity of the heat transfer sheet can be used. Specifically, in order to adjust the thermal resistance between the heat transfer sheet 12 connecting the heat source portion 10 and the temperature control section 11a close to the heat source portion 10, the thermal resistance can be adjusted by using a material with a low thermal conductivity for the heat transfer sheet, reducing the thickness or the width of the heat transfer sheet, or changing the shape of the heat transfer sheet in two dimensions or three dimensions.

Since the heat transfer sheets 12 are stacked with each other, the heat transfer sheets 12 can be formed in a compact shape and installed in a narrow place.

The heat transfer sheet 12 is made of a sheet-shaped material having high thermal conductivity. As a high thermal conductivity material, metallic materials other than a carbon material can be used. As a carbon material, it is possible to use a sheet made of carbon fiber, carbon nanotube, graphene, diamond or the like in addition to a graphite sheet. As the metal, it is possible to use a single metal such as gold, silver, aluminum, copper or an alloy of these metals.

When an anisotropic heat conductive material, which is likely to transfer heat in a direction parallel to the sheet surface (a left-right direction and a thickness direction of the drawing paper) compared to in a direction perpendicular to the sheet surface (an up-down direction in the drawing), is used as the material of the heat transfer sheet 12, the effects in the up-down direction can be reduced, and accordingly the heat can be effectively transferred between the temperature control surface 11a and the heat source portion 10. As the degree of anisotropy of the thermal conductivity, the thermal conductivity in the direction parallel to the sheet surface is 10 times or more, more preferably 100 or more times larger than the thermal conductivity in the direction orthogonal to the sheet surface. The heat conductivity of the heat transfer sheet 12 is higher in the direction parallel to the sheet surface, that is, in the direction connecting the heat source portion 10 and the temperature control section 11a than the heat conductivity in at least one other direction.

Examples of such high thermal conductivity materials include graphite sheets such as Graphinity (manufactured by Kaneka), PGS graphite sheets (manufactured by Panasonic), and GD-AGS (manufactured by Guardneck). In the present embodiment, Graphinity (40 μm in thickness) manufactured by Kaneka is used as the high thermal conductivity material. The thermal conductivity of the Kaneka Graphinity of the present embodiment in the direction parallel to the sheet surface is 1500 W/mK, the thermal conductivity in the direction perpendicular to the sheet surface is 5 W/mK. The thermal conductivity in the direction parallel to the sheet surface is 300 times larger than the thermal conductivity in the direction perpendicular to the sheet surface.

One graphite sheet may be used as one heat transfer sheet 12, and some graphite sheets may be stacked to be used as one heat transfer sheet 12. When some graphite sheets are stacked and used as one heat transfer sheet 12, the heat conductivity of the heat transfer sheet 12 can be increased.

The heat transfer sheets 12 are stacked with each other. Thermal insulation sheets 13 are disposed between the adjacent heat transfer sheets 12, and the thermal insulation sheets 13 and the heat transfer sheet 12 are alternately stacked with each other. The heat insulation sheet 13 covers the heat transfer sheet 12. The heat insulation sheet 13 is a sheet-shaped heat insulating material, and for example, foamed urethane, foamed olefin, foamed resin such as foamed acrylic, glass wool, or ceramic fiber such as silica wool can be used as the heat insulation sheet 13. In the present embodiment, Marinetex Cross (thickness: 0.18 mm) manufactured by Nichias or LZ-2000 (thickness: 0.9 mm) manufactured by Inoac is used as the heat insulation sheet 13. The heat insulation sheet 13 corresponds to the heat insulation portion of the present disclosure.

The heat insulation sheet 13 makes it difficult to transfer heat between the respective heat transfer sheets 12. In addition to the effect that it is possible to directly transfer hot heat or cold heat of the heat source portion 10 to the temperature control section 11a by the heat transfer sheet 12 as described above, desired temperature control can be performed without being affected by the temperature change of another temperature control section 11a even when the temperature of an object (for example, a human body) in contact with is different in each temperature control section 11a.

Figure 2:
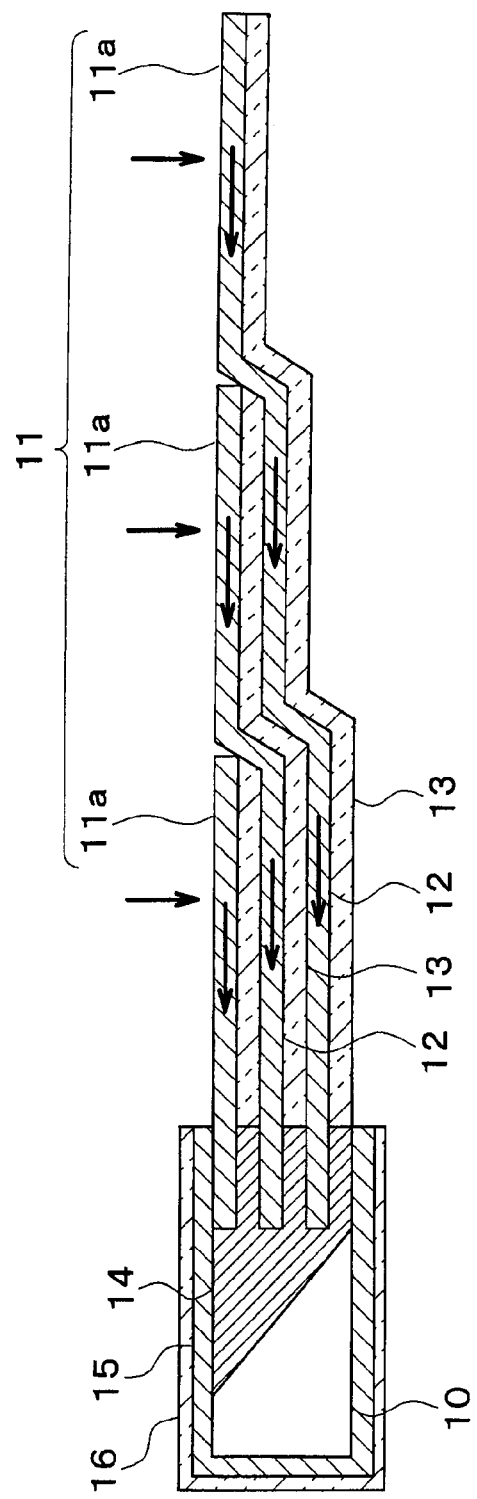
FIG. 2 is a cross-sectional diagram illustrating a flow of heat in the heat conduction device of at least one embodiment of the present disclosure.

As shown to FIG. 1 and FIG. 2, the heat transfer sheet 12 and the heat insulation sheet 13 are bent in one part or several parts according to these thicknesses. Thus, in the present embodiment, the temperature control sections 11a are located on the same plane.

By using a flexible material as a constituent material of the heat transfer sheet 12 and the heat insulation sheet 13, it is possible to form a curved surface as well as bending and twisting. As a flexible material of the heat transfer sheet 12, thin metal plate can be used as well as carbon materials such as graphite sheet. Moreover, foamed resin, glass wool, or ceramic fibers such as silica wool may be used as a flexible material of the heat insulation sheet 13.

The heat source portion 10 and the thermal resistance adjuster 14 are accommodated in a casing 15. The casing 15 is covered with a heat source heat insulation portion 16. The casing 15 may be made of the material that is the same as the thermal resistance adjuster 14, for example. When the casing 15 and the thermal resistance adjuster 14 are made of the same material, the casing 15 and the thermal resistance adjuster 14 may be provided as a single component.

The material of the heat source heat insulation portion 16 may be the same as that of the heat insulation sheet 13. Since the heat source heat insulation portion 16 suppress the heat dissipation from the heat source portion 10 and the thermal resistance adjuster 14 to the outside, the amount of heat that is transferred from the heat source portion 10 to the temperature control sections 11a can be increased. The heat source heat insulation portion 16 is not necessarily required when the heat of the heat source portion 10 can be transferred to the temperature control surface 11 sufficiently.

The heat transfer sheets 12 and the heat insulation sheets 13 may be bonded with each other by adhesive to laminate the heat transfer sheets 12 and the heat insulation sheets 13. In this case, the sheets 12, 13 may be bonded over the entire surface, or the sheets 12, 13 may be partially bonded.

When the sheets 12 and 13 are partially adhered, for example, the portions of the sheets 12 and 13 accommodated in the casing 15 are adhered to each other, and the portions of the sheets 12 and 13 outside the casing 15 are not adhered to each other. When the sheets 12, 13 are partially adhered to each other, the laminate formed of the heat transfer sheets 12 and the heat insulation sheets 13 is more flexible than in the case where the respective sheets 12, 13 are adhered over the entire surface.

In FIG. 2, flows of the heat in a case where the heat source portion 10 supplies cold heat to cool the human body in contact with the temperature control surface 11 are illustrated. In the example shown in FIG. 2, the temperature control surface 11 are sectioned into three temperature control sections 11a based on the distance from the heat source portion 10. As shown in FIG. 2, the heat of the human body moves from the temperature control sections 11a to the heat source portion 10 through the heat transfer sheets 12. Thereby, the human body in contact with the temperature control sections 11a is cooled by the cold heat of the heat source portion 10.

TABLE 1

| Distance (cm) | 1 | 3 | 5 | 7 | 9 | 11 | 13 | 15 | 17 | 19 |
|---|---|---|---|---|---|---|---|---|---|---|
| Embodiment (° C.) | 16.3 | 16.7 | 16.9 | 17.6 | 18.0 | 18.7 | 19.6 | 20.7 | 21.7 | 23.0 |
| Comparative example (° C.) | 17.9 | 19.9 | 22.5 | 23.3 | 24.2 | 24.6 | 25.0 | 25.2 | 25.3 | 25.3 |

Figure 3:
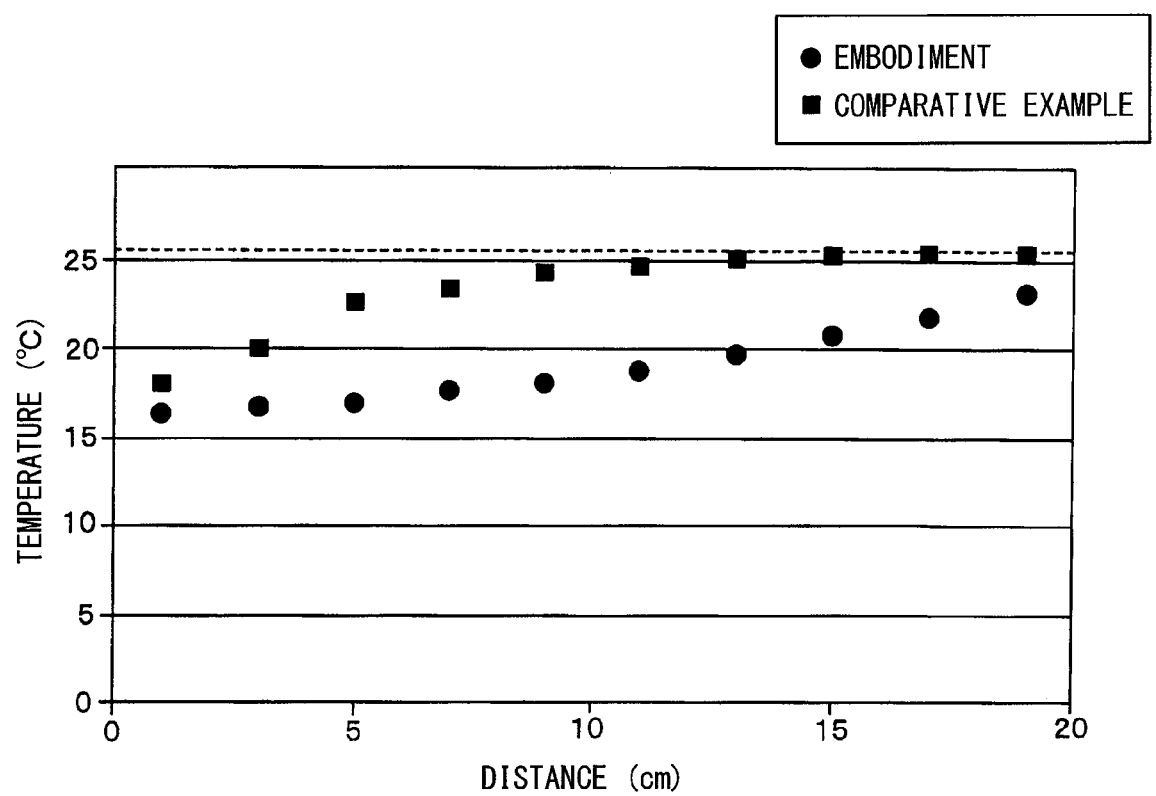
FIG. 3 is a graph illustrating a relationship between a surface temperature of a temperature control surface and a distance between the temperature control surface and a heat source portion.
Figure 4:
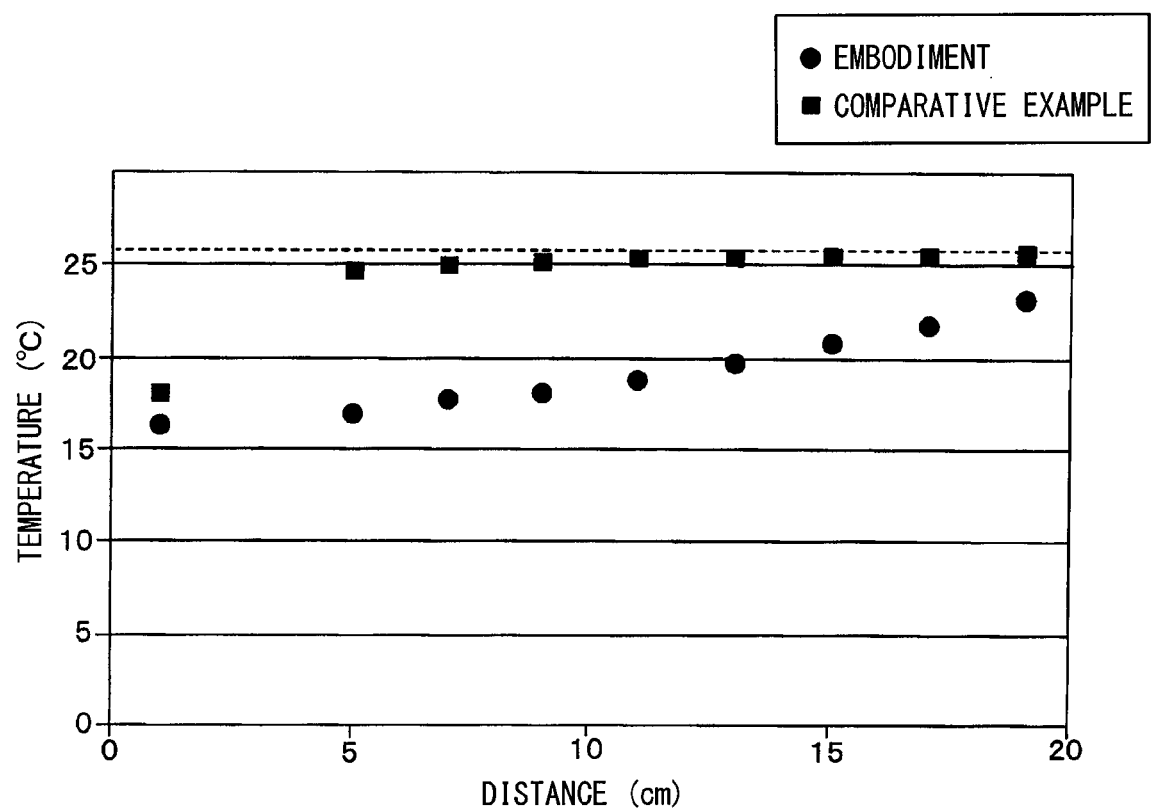
FIG. 4 is a graph illustrating a relationship between a surface temperature of a temperature control surface and a distance between the temperature control surface and a heat source portion.

FIG. 3 and Table 1 show relationships between a surface temperature of the temperature control surface 11 and the distance between the temperature control surface 11 and the heat source portion 10. In the example shown in FIG. 3 and Table 1, the temperature of the heat source portion 10 is 5 degrees Celsius, and the outside air temperature is 26 degrees Celsius. In FIG. 3 and Table 1, a configuration in which the temperature control surface 11 is not sectioned is shown as a comparative example. In FIGS. 3, 4, 26 degrees Celsius is indicated by a dotted line.

As shown in FIG. 3 and Table 1, in the comparative example in which the temperature control surface 11 is formed as single surface, the increase rate of the surface temperature of the temperature control surface 11 is high, and accordingly the surface temperature rapidly approaches the outside air temperature with the distance from the heat source portion 10. In contrast, in the present embodiment in which the temperature control surface 11 is divided into the temperature control sections 11a, the surface temperature of the temperature control surface 11 gradually increases. For this reason, in the present embodiment, the surface temperature of the temperature control surface 11 is maintained at a low level even at a part disposed away from the heat source portion 10 to some extent. That is, in the present embodiment, it is possible to effectively transfer the cold heat of the heat source portion 10 to a place away from the heat source portion 10.

TABLE 2

| Distance (cm) | 1 | 3 | 5 | 7 | 9 | 11 | 13 | 15 | 17 | 19 |
|---|---|---|---|---|---|---|---|---|---|---|
| Embodiment (° C.) | 16.3 | — | 16.9 | 17.6 | 18.0 | 18.7 | 19.6 | 20.7 | 21.7 | 23.0 |
| Comparative example (° C.) | 17.9 | — | 24.5 | 24.8 | 25.0 | 25.2 | 25.2 | 25.3 | 25.3 | 25.5 |

FIG. 4 and Table 2 show the relationships between the surface temperature of the temperature control surface 11 and the distance from the heat source portion 10 of the temperature control surface 11 when a human body is in contact with a part of the temperature control surface 11. In the example shown in FIG. 4 and Table 2, the human body is in contact with a part of the temperature control surface 11 3 cm away from the heat source portion 10. Also in the example shown in FIG. 4 and Table 2, the temperature of the heat source portion 10 is 5 degrees Celsius, and the outside temperature is 26 degrees Celsius. A configuration in which the temperature control surface 11 is not divided is shown as a comparative example.

As shown in FIG. 4 and Table 2, in the comparative example where the temperature control surface 11 is formed as single surface, the surface temperature rapidly increases at a part father from the heat source portion 10 than the part where the human body is in contact. That is, in the comparative example, although the cold heat of the heat source portion 10 can be transferred to the human body in contact with the temperature control surface 11, the cold heat of the heat source portion 10 is unlikely to be transferred to a part farther from the part in contact with the human body due to the heat of the human body. When a portion of the human body whose area is larger than a certain area is in contact with the temperature control surface 11, the user feels the hot heat or cold heat at a part close to the heat source. However, the user may not sufficiently feel the hot heat or the cold heat at the other part farther from the heat source due to the heat transfer at the part close to the heat source.

In contrast, in the present embodiment, each temperature control section 11a of the temperature control surface 11 is independently connected to the heat source portion 10 through the heat transfer sheet 12. Accordingly, even when the human body is in contact with a part of the temperature control surface 11, the other part of the temperature control surface 11 is unlikely to be affected. For this reason, in the present embodiment, the surface temperature of the temperature control surface 11 is maintained at a low level even at a part farther from the heat source portion 10 than the part in contact with the human body. That is, according to the present embodiment, the cold heat can be transferred to the human body in contact with a part of the temperature control surface 11. In addition, the cold heat of the heat source portion 10 can be effectively transferred to the other part farther from the heat source portion 10 than the part at which the human body is in contact with the temperature control surface 11. As a result, the temperature of the temperature control surface 11 can be uniformed without being influenced by the disturbance factor generated on the temperature control surface 11.

According to the present embodiment described above, the temperature control surface 11 is divided into temperature control sections 11a based on the distance from the heat source portion 10, and the respective temperature control section 11a and the heat source portion 10 are connected through heat transfer sheet 12. Thus, regardless of the distance from the heat source portion 10, the temperature control sections 11a can be directly heated or cooled by the heat of the heat source portion 10. Therefore, the temperature control section 11a disposed away from the heat source portion 10 can also be heated or cooled in the same manner as the temperature control section 11a disposed near the heat source portion 10, and the entire temperature control surface 11 can be adjusted to a uniform temperature.

Further, according to the configuration of the present embodiment, even when a thermal disturbance, such as a contact of a human body with the temperature control surface 11, that occurs heat exchange between the temperature control surface 11 and the outside is occurred, the temperature of the temperature control surface 11 can be uniformed.

Moreover, in the present embodiment, as described above, since the flex material is used for the heat transfer sheet 12, it is possible to form an appropriate curved surface even in contact with the human body, and accordingly the comfort is not impaired.

Second Embodiment

Next, a second embodiment of the present disclosure will be described. In the first embodiment described above, the thermal resistance between the heat source portion 10 and the temperature control sections 11a is adjusted by the thermal resistance adjuster 14. In the second embodiment, the thermal resistance between the heat source portion 10 and the temperature control sections 11a is adjusted by changing the shape or the material of the heat transfer sheets 12.

Figure 5:
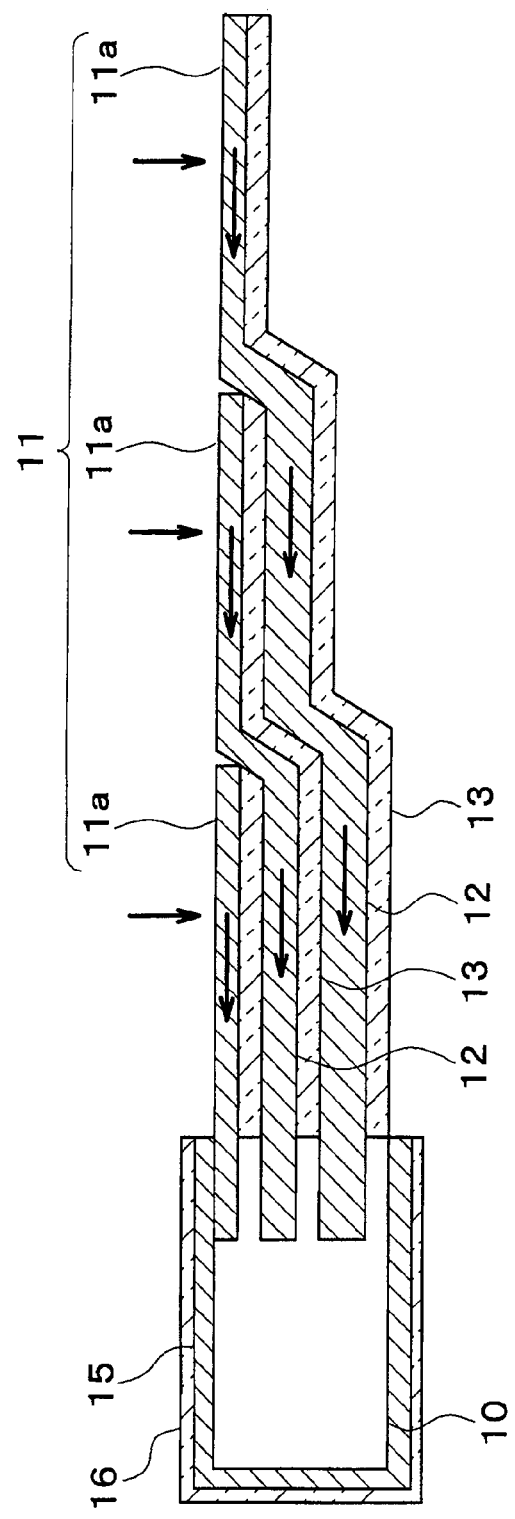
FIG. 5 is a cross-sectional diagram illustrating a heat conduction device according to at least one embodiment of the present disclosure.

In FIG. 5, an example where the thicknesses of the heat transfer sheets 12 are varied is shown. When the thicknesses of the heat transfer sheets 12 are varied as shown in FIG. 5, the thermal resistance of the heat transfer sheet 12 can be decreased by making the heat transfer sheet 12 thick, and the thermal resistance of the heat transfer sheet 12 can be increased by making the heat transfer sheet 12 thin.

Moreover, although illustration is omitted, the widths of the heat transfer sheets 12 may be varied, and the material of the heat transfer sheet 12 may be varied. When the widths of the heat transfer sheets 12 are varied, the thermal resistance can be decreased by increasing the width of the heat transfer sheet 12, and the thermal resistance can be increased by decreasing the width of the heat transfer sheet 12. When the materials of the heat transfer sheets 12 are varied, the thermal resistance can be reduced by using a material having a large thermal conductivity, and the thermal resistance can be increased by using a material having a small thermal conductivity.

Since the thermal resistance between the heat source portion 10 and the temperature control sections 11a is uniformed by the heat transfer sheet 12 itself in the second embodiment, the adjustment of the thermal resistance by the thermal resistance adjuster 14 is not necessary, and accordingly the thermal resistance adjuster 14 is not needed. Therefore, direct heat exchange can be performed between the heat source portion 10 and the heat transfer sheet 12.

When the heat transfer sheet 12 uniforms the thermal resistance between the heat source portion 10 and the temperature control sections 11a as in the second embodiment, the heat transfer sheet 12 has the same function as the thermal resistance adjuster 14. The adjustment of the thermal resistance by the heat transfer sheet 12 and the adjustment of the thermal resistance by the thermal resistance adjuster 14 may be used together to mutually complement the function of adjusting the temperature control surface 11 to a uniform temperature.

Third Embodiment

Next, a third embodiment of the present disclosure will be described. In the first embodiment described above, the thermal resistance between the heat source portion 10 and the temperature control sections 11a is adjusted by the thermal resistance adjuster 14. In the third embodiment, the temperature control sections 11a are provided based on the thermal resistance between the heat source portion 10 and the temperature control section 11a. For example, the area of the temperature control section 11a may be varied based on the thermal resistance between the heat source portion 10 and the temperature control section 11a.

Figure 6:
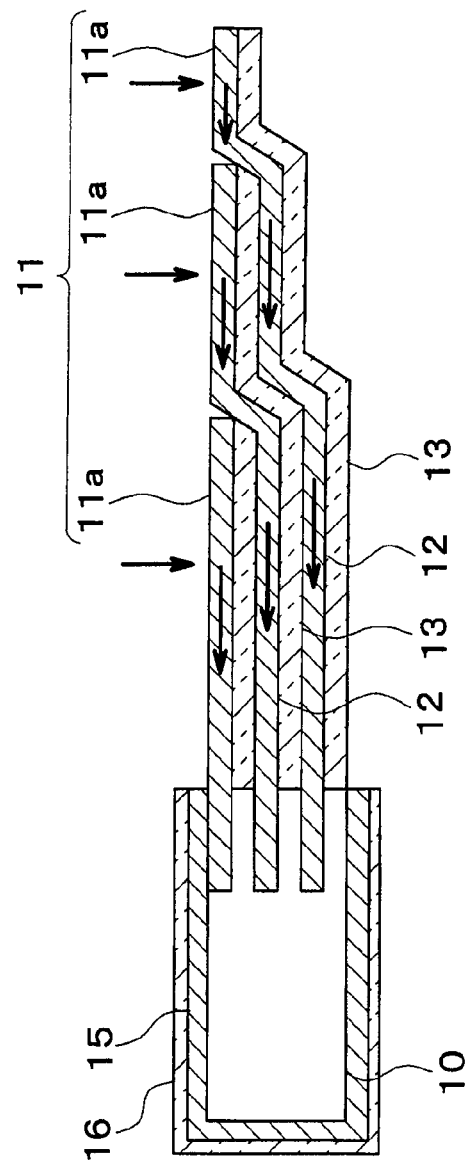
FIG. 6 is a cross-sectional diagram illustrating a heat conduction device according to at least one embodiment of the present disclosure.

In FIG. 6, an example where the area of the temperature control section 11a is varied based on the thermal resistance between the heat source portion 10 and the temperature control section 11a. As shown in FIG. 6, when the thermal resistance between the heat source portion 10 and the temperature control section 11a is large, the area of the temperature control section 11a is small. When the thermal resistance between the heat source portion 10 and the temperature control section 11a is small, the area of the temperature control section 11a is large. Specifically, the area of the temperature control section 11a far from the heat source portion 10 is small, and the area of the temperature control section 11a close to the heat source portion 10 is large.

To vary the area of the temperature control sections 11a, the length of the temperature control section 11a in a left-right direction in FIG. 6 may be adjusted as shown in FIG. 6, or the length of the temperature control section 11a in a direction perpendicular to the drawing sheet of FIG. 6 may be adjusted.

In these cases, similarly to the second embodiment, since the thermal resistance between the heat source portion 10 and the temperature control sections 11a is uniformed by the temperature control section 11a itself, the adjustment of the thermal resistance by the thermal resistance adjuster 14 is not necessary, and accordingly the thermal resistance adjuster 14 is not needed. Therefore, direct heat exchange can be performed between the heat source portion 10 and the heat transfer sheet 12.

When the temperature control section 11a uniforms the thermal resistance between the heat source portion 10 and the temperature control sections 11a as in the third embodiment, the heat transfer sheet 12 has the same function as the thermal resistance adjuster 14. Similarly to the second embodiment, the adjustment of the thermal resistance by the temperature control section 11a and the adjustment of the thermal resistance by the thermal resistance adjuster 14 may be used together to mutually complement the function of adjusting the temperature control surface 11 to a uniform temperature.

Fourth Embodiment

Next, a fourth embodiment of the present disclosure will be described. In the above-described first embodiment, the temperature control sections 11a adjacent to each other are located on one plane by bending the heat transfer sheets 12 and the heat insulation sheets 13. In the fourth embodiment, the heat transfer sheets 12 and the heat insulation sheets 13 extend straight to have a flat shape.

Figure 7:
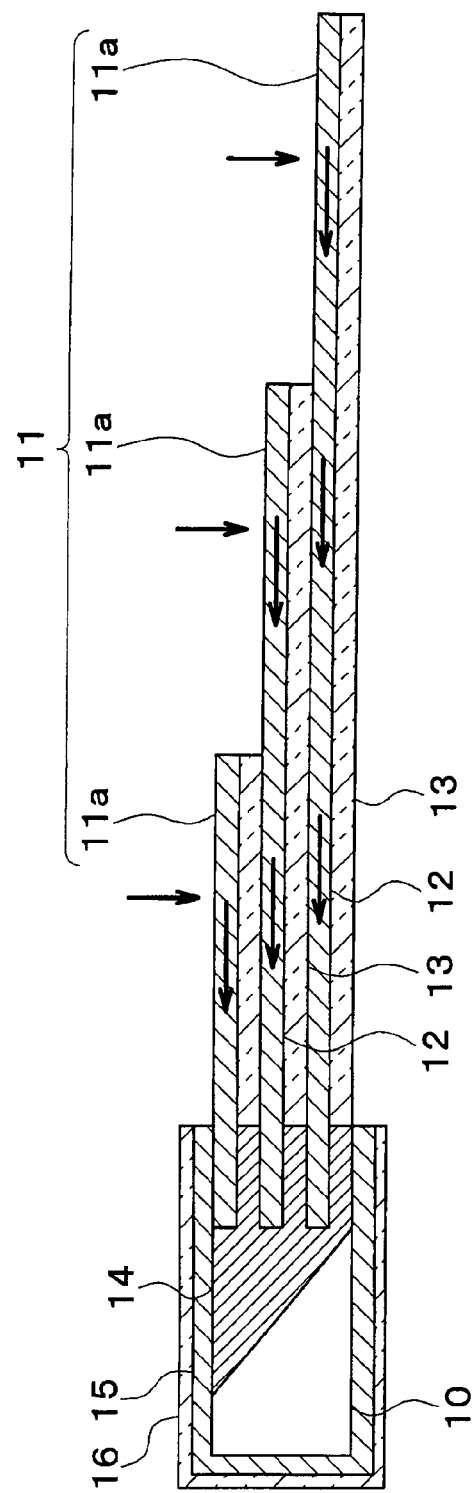
FIG. 7 is a cross-sectional diagram illustrating a heat conduction device according to at least one embodiment of the present disclosure.

As shown in FIG. 7, when the heat transfer sheets 12 and the heat insulation sheets 13 have a flat shape, steps are provided between the temperature control sections 11a adjacent to each other. The steps are formed between the temperature control sections 11a adjacent to each other in the fourth embodiment. However, when the heat transfer sheets 11a and the heat insulation sheets 13 are sufficiently thin, the user senses the temperature control surface 11 as a flat surface or a curved surface without sensing the steps even when the steps are formed between the temperature control sections 11a. In addition, depending on the application of the heat conduction device 1, there may be no problem even if the user senses the steps provided between the temperature control sections 11a.

Fifth Embodiment

Next, a fifth embodiment of the present disclosure will be described. In the fifth embodiment, a heat transfer path between the heat source portion 10 and the temperature control sections 11a can be switched between a connected state and a disconnected state in the configurations of the above-described embodiments. For example, the heat transfer path is configured to be able to be separated, and thus the heat transfer path between the heat source portion 10 and the temperature control section 11a can be connected and disconnected by mechanically switching the heat transfer sheet 12 between the connected state and disconnected state. Thereby, on/off control of heat transfer between the heat source portion 10 and the temperature control sections 11a can be performed.

Figure 8:
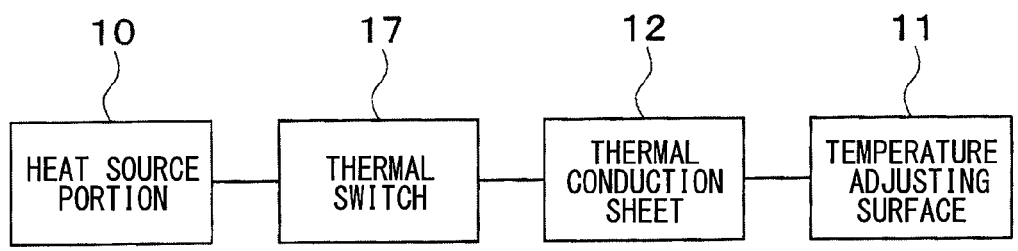
FIG. 8 is a block diagram illustrating a configuration of a heat conduction device including a thermal switch, according to at least one embodiment of the present disclosure.
Figure 9:
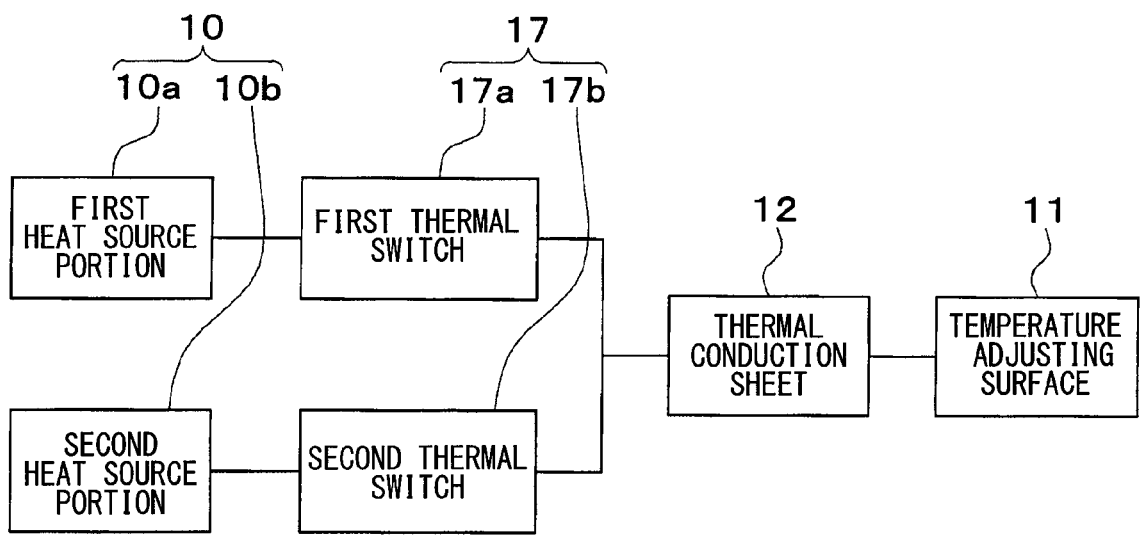
FIG. 9 is a block diagram illustrating a configuration of the heat conduction device including thermal switches, according to at least one embodiment of the present disclosure.

Specifically, as shown in FIGS. 8, 9, a thermal switch 17 configured to control the heat transfer is inserted between the heat source portion 10 and the heat transfer sheet 12. The thermal switch 17 is a switch configured to switch between the heat conductive state and the heat insulated state between the heat source portion 10 and the heat transfer sheet 12. By using the thermal switch 17, unnecessary heat transfer from the heat source portion 10 to the heat transfer sheet 12 can be suppressed, or the heat transferred from the heat source portion 10 to the heat transfer sheet 12 can be increased drastically.

A well-known structure can be used as the heat switch 17 such as thermal switches described in WO 2014/156991 A1 or JP 2015-092101 A.

An example where the thermal switch 17 is provided between the heat source portion 10 and the heat transfer sheet 12 is shown in FIG. 8. When the heat transfer from the heat source portion 10 to the heat transfer sheet 12 is not necessary, the unnecessary heat transfer can be suppressed by shutting off the heat transfer path by the thermal switch 17.

An example where two heat source portions 10a, 10b are provided is shown in FIG. 9. For example, a first heat source portion 10a is used as a hot heat source, and a second heat source portion 10b is used as a cold heat source. A first thermal switch 17a is provided between the first heat source portion 10a and the heat transfer sheet 12, and a second thermal switch 17b is provided between the second heat source portion 10b and the heat transfer sheet 12. According to the configuration shown in FIG. 9, the heat source portions 10a, 10b connected to the heat transfer sheet 12 can be switched by using two thermal switches 17a, 17b, and accordingly the temperature of the temperature control surface 11 can be changed quickly.

Bonding between the respective components shown in FIGS. 8, 9 can be performed by a method providing a good thermal connection such as brazing, soldering, and screwing. Further, the respective components may be connected by heat pipes. Furthermore, the first heat source portion 10a (hot heat source) in FIG. 9 can also be configured by a Peltier device. In that case, the first heat source portion 10a is electrically controlled, and the first heat switch 17a is not necessary.

Sixth Embodiment

Next, a sixth embodiment of the present disclosure will be described. The sixth embodiment is different from the first embodiment in the configurations of the heat transfer sheet 12 and the thermal resistance adjuster 14.

In the above-described first embodiment, the thermal resistance adjuster 14 is provided between the heat source portion 10 and the heat transfer sheet 12. However, in the sixth embodiment, the heat transfer sheet 12 is separated, and the thermal resistance adjuster 14 is provided between the separated heat transfer sheets 12. For this reason, in the sixth embodiment, the heat source portion 10 and the heat transfer sheet 12 are in direct contact with each other, and direct heat exchange can be performed between the heat source portion 10 and the heat transfer sheet 12.

Figure 10:
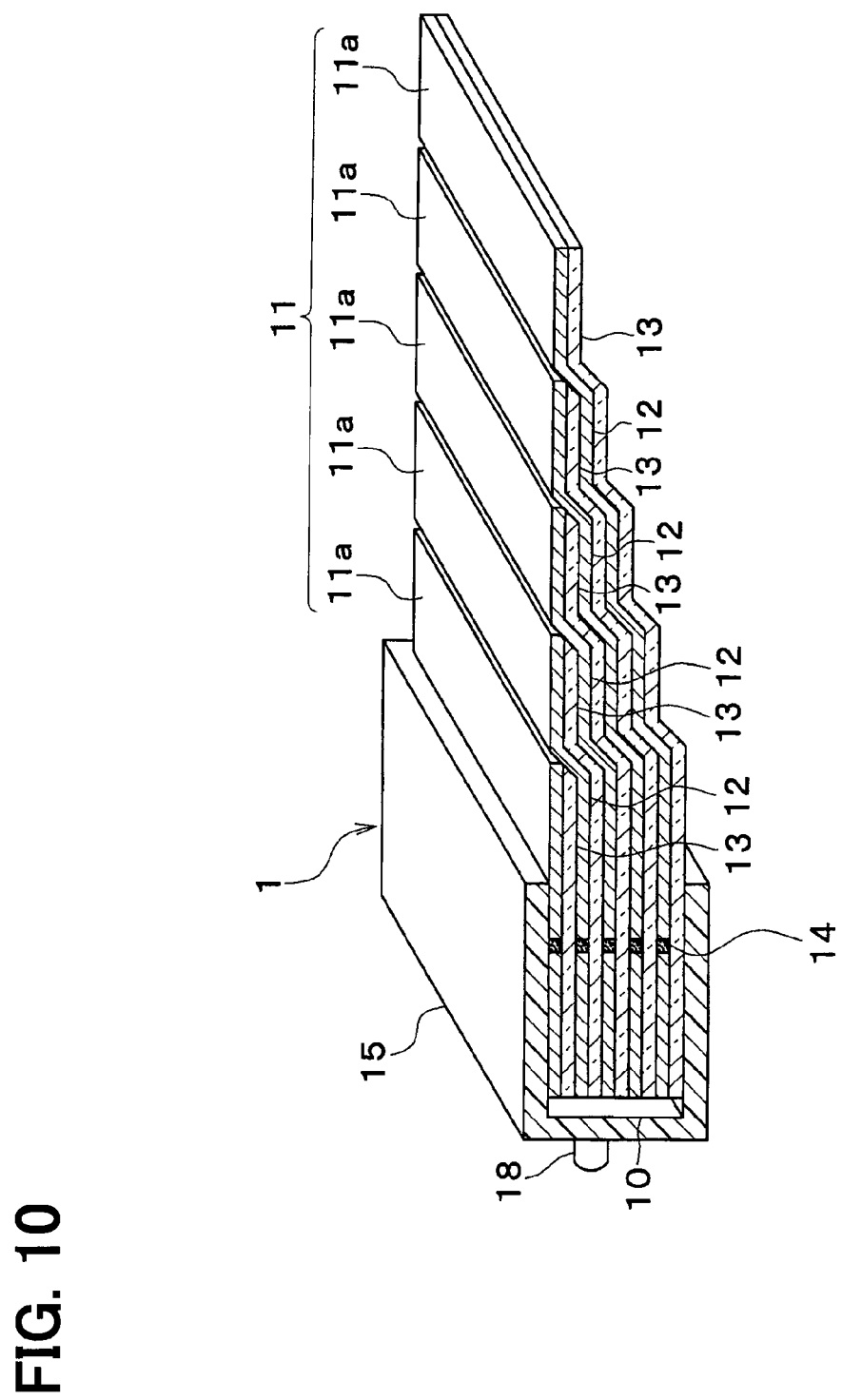
FIG. 10 is a perspective view illustrating a heat conduction device according to at least one embodiment of the present disclosure.

As shown in FIG. 10, in the sixth embodiment, multiple thermal resistance adjusters 14 are provided to correspond to multiple heat transfer sheets 12. In an example shown in FIG. 10, the heat transfer sheet 12 is separated into two pieces, and the thermal resistance adjuster 14 is provided between the separated heat transfer sheets 12. The heat is transferred between the separated heat transfer sheets 12 through the thermal resistance adjuster 14. The material of the thermal resistance adjuster 14 has a thermal conductivity lower than the heat transfer sheet 12. In the sixth embodiment, the size of each of the thermal resistance adjusters 14 is the same.

Figure 11:
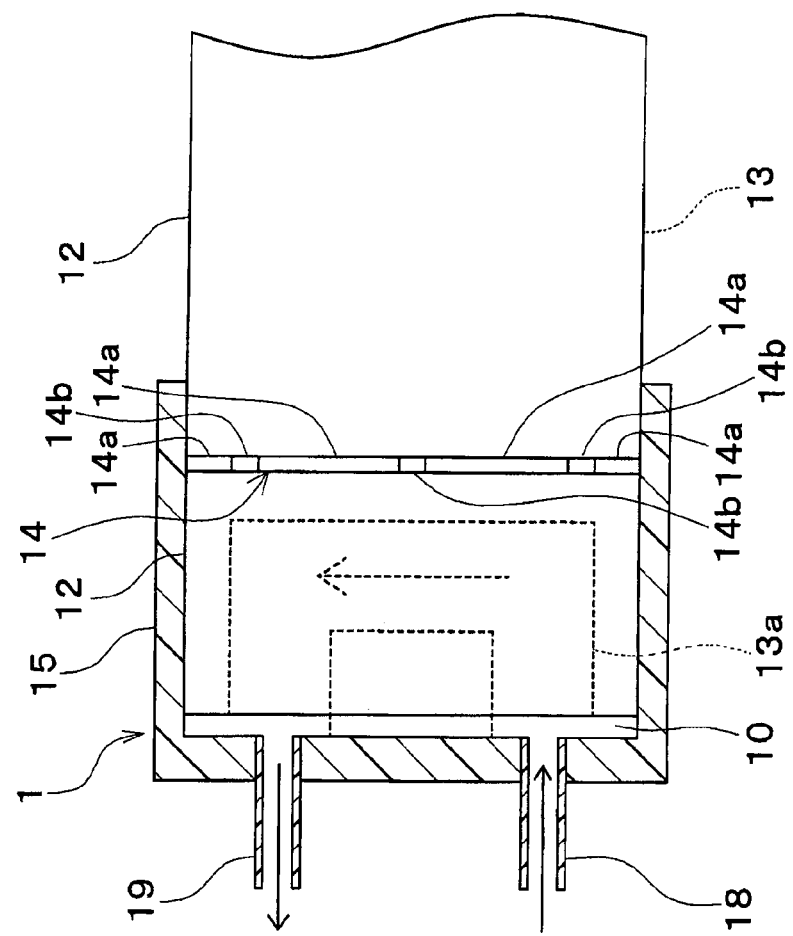
FIG. 11 is a cross-sectional view of the heat conduction device of at least one embodiment of the present disclosure.

FIG. 11 is an upper view of a cross section of the heat conduction device 1 taken at the position of the heat transfer sheet 12. As shown in FIG. 11, the thermal resistance adjuster 14 of the sixth embodiment includes multiple adjusters 14a, 14b. The adjusters 14a, 14b are made of different materials having different thermal conductivities.

In the sixth embodiment, the first adjuster 14a is made of TIM (Thermal Interface Material), and the second adjuster 14b is made of PET resin. The thermal conductivity of the TIM is about 10 W/mK, and the thermal conductivity of the PET resin is about 0.1 W/mK.

Since the TIM constituting the first adjustment portion 14a is a paste-like material having adhesiveness, it is easy to fill the gaps between the separated heat transfer sheets 12, and accordingly it is possible to suppress the formation of gaps between the heat transfer sheet 12 and the thermal resistance adjuster 14. In addition, since the TIM material has flexibility, it can form an appropriate curved surface even in contact with the human body in combination with the heat transfer sheet 12 having flexibility, and accordingly comfort is not impaired.

The thermal conductivity can be adjusted by adjusting the ratio between the first adjuster 14a and the second adjuster 14b. Specifically, the thermal conductivity can be increased by increasing the proportion of the first adjuster 14a, and the thermal conductivity can be decreased by increasing the proportion of the second adjuster 14b. In the sixth embodiment, as the heat transfer sheet 12 is longer, the proportion of the first adjuster 14a in the thermal resistance adjuster 14 is increased to increase the thermal conductivity. Moreover, as the heat transfer sheet 12 is shorter, the proportion of the second adjuster 14b in the thermal resistance adjuster 14 is increased to decrease the thermal conductivity.

In the sixth embodiment, the casing 15 is made of an acrylic resin which is a nonmetal material. The casing 15 has an inlet 18 through which the cooling water flows into the heat source portion 10 from the outside, and an outlet 19 through which the cooling water flows out of the heat source portion 10 to the outside. Moreover, the casing 15 and the heat transfer sheet 12 are joined by the adhesive or the adhesive agent.

As indicated by a dashed line in FIG. 11, the heat insulation sheet 13 is provided with a groove 13a. The groove 13a of the heat insulation sheet 13 and the heat transfer sheets 12 located on both sides of the heat insulation sheet 13 define a hollow space. The groove 13a has a U-shape and communicates with the heat source portion 10. For this reason, the cooling water of the heat source portion 10 flows through the groove 13a. Thereby, the contact area of the heat source portion 10 and the heat transfer sheet 12 can be increased.

According to the sixth embodiment described above, the heat transfer sheet 12 is divided into multiple parts, and the thermal resistance adjuster 14 is disposed between the separated heat transfer sheets 12. Also by such a configuration, differences of the thermal resistance due to the difference of the lengths of the heat transfer sheets 12 can be adjusted. Thereby, the thermal resistance between the heat source portion 10 and each temperature control section 11a can be uniformed, and the temperature distribution generated on the temperature control surface 11 can be uniformed.

In the sixth embodiment, the thermal resistance of the thermal resistance adjuster 14 can be adjusted by using the adjusters 14a, 14b made of different materials and by adjusting the ratio between the adjusters 14a, 14b. In the configuration of the sixth embodiment, the thermal resistance adjuster 14 may be made of single material. When the thermal resistance adjuster 14 is made of single material, the thermal resistance of the thermal resistance adjuster 14 can be adjusted by adjusting the size or the shape of the thermal resistance adjuster 14. For example, the thermal resistance of the thermal resistance adjuster 14 can be adjusted by varying the widths of the thermal resistance adjuster 14 sandwiched between the separated heat transfer sheets 12.

In the sixth embodiment, the heat source portion 10 is directly in contact with the heat transfer sheet 12. Accordingly, the heat can be directly exchanged between the heat source portion 10 and the heat transfer sheet 12, and the heat of the heat source portion 10 can be efficiently transferred to the heat transfer sheet 12.

In the sixth embodiment, the groove 13a communicating with the heat source portion 10 is provided in the heat insulation sheet 13. Accordingly, the contact area of the heat source portion 10 and the heat transfer sheet 12 can be increased, and the heat can be efficiently exchanged between the heat source portion 10 and the heat transfer sheet 12.

The amount of heat transferred from the heat source portion 10 to the heat transfer sheet 12 may be adjusted by adjusting the contact area of the heat source portion 10 with the heat transfer sheet 12 by varying the size of the groove 13a of the heat insulation sheet 13. Specifically, the amount of the heat transferred from the heat source portion 10 to the heat transfer sheet 12 can be increased by increasing the size of the groove 13a of the heat insulation sheet 13, and the amount of the heat transferred from the heat source portion 10 to the heat transfer sheet 12 can be decreased by decreasing the size of the groove 13a of the heat insulation sheet 13. Therefore, the groove 13a of the heat insulation sheet 13 is enlarged as the heat transfer sheet 12 is longer, and the groove 13a of the heat insulation sheet 13 is smaller as the heat transfer sheet 12 is shorter.

Further, in the sixth embodiment, the casing 15 is made of a nonmetal material. Thereby, the following effects can be obtained.

When the thermal resistance adjuster 14 and the casing 15 are integrally formed of a metal material in the first embodiment, the thermal resistance adjuster 14, the casing 15, and the heat transfer sheet 12 are bonded by using silver paste having a high thermal conductivity. In this case, a heating process is required for bonding, and the thermal resistance adjuster 14 and the casing 15 made of a metal material and the heat transfer sheet 12 made of a graphite sheet are easily peeled off.

In contrast, in the sixth embodiment, the heat source portion 10 and the heat transfer sheet 12 are directly in contact with the heat transfer sheet 12. Accordingly, the silver paste for bonding of the casing 15 and the heat transfer sheet 12 are not needed, and the casing 15 and the heat transfer sheet 12 can be bonded by using an adhesive. For this reason, a heating process is unnecessary for joining of the casing 15 and the heat transfer sheet 12, and the casing 15 and the heat transfer sheet 12 are unlikely to peel off.

Further, the weight of the heat conduction device 1 can be reduced by using the acrylic resin which is a nonmetallic material as a material of the casing 15.

Seventh Embodiment

Next, a seventh embodiment of the present disclosure will be described. In the seventh embodiment, the thermal resistance between the heat source portion 10 and the temperature control section 11a is adjusted by varying the shapes of the heat transfer sheets 12.

Figure 12:
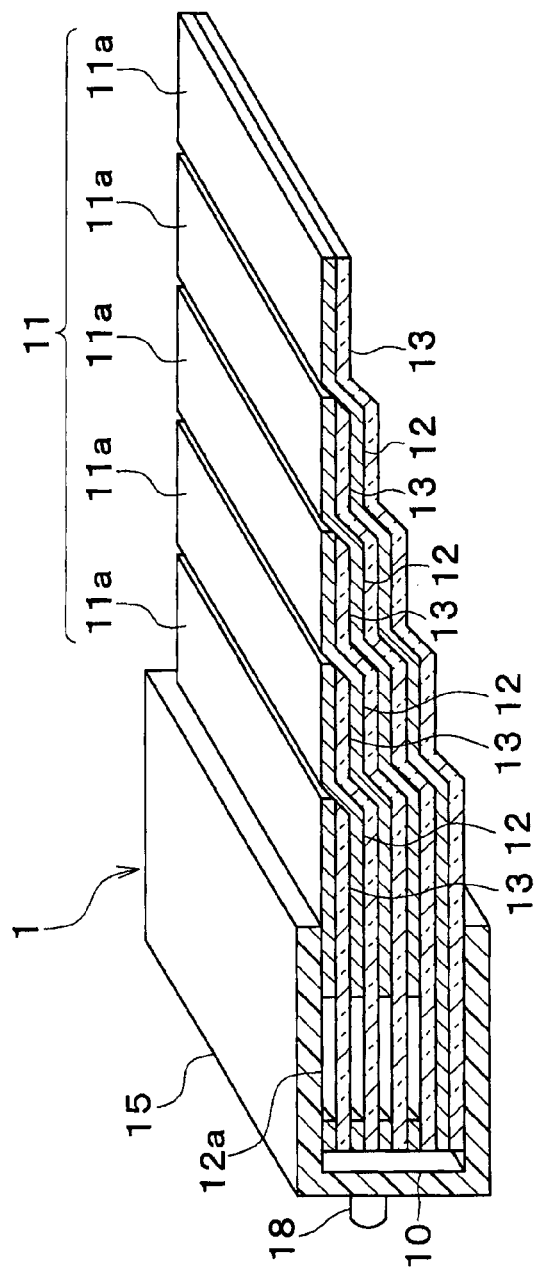
FIG. 12 is a perspective view illustrating a heat conduction device according to at least one embodiment of the present disclosure.
Figure 13:
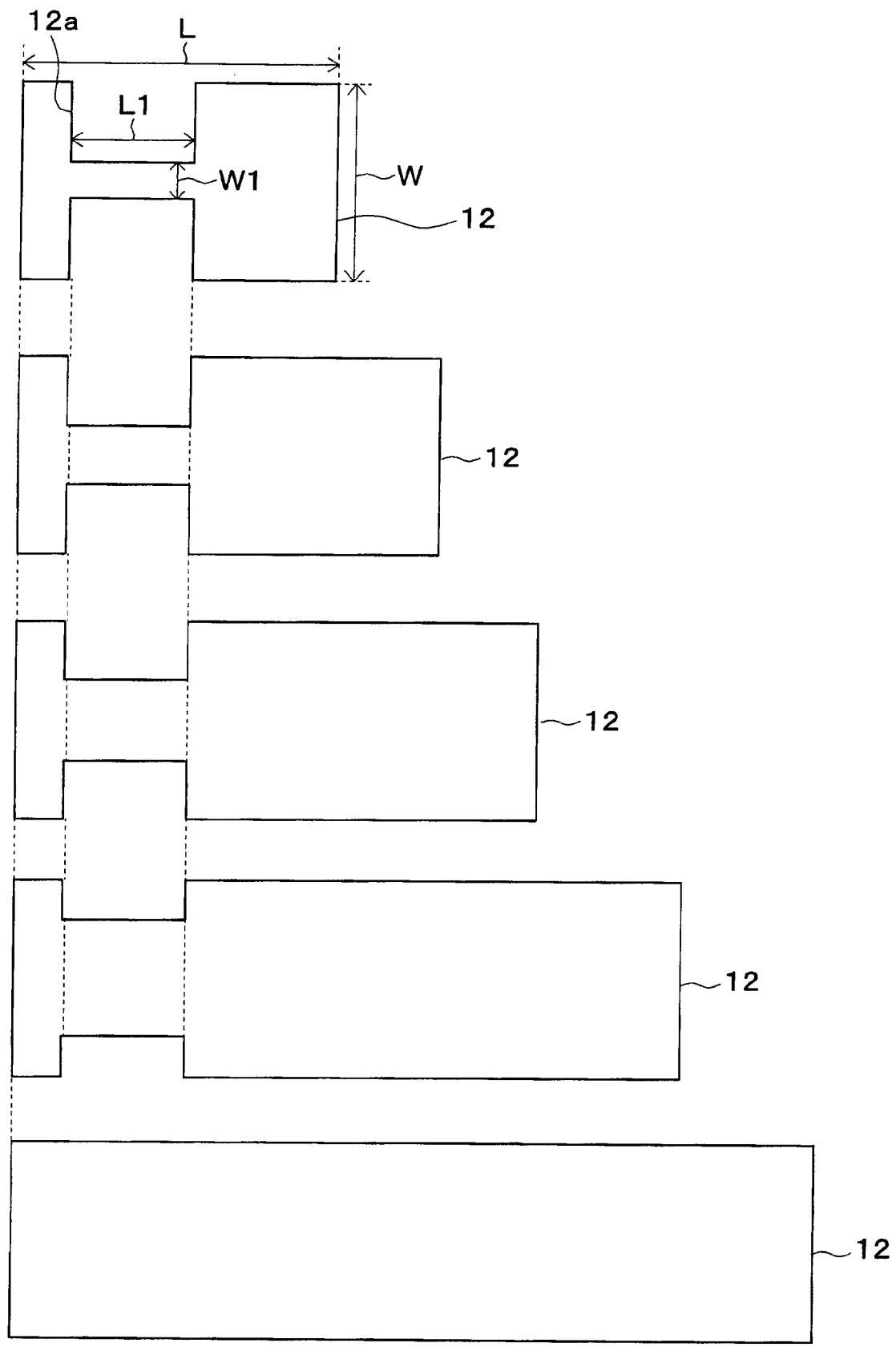
FIG. 13 is a plan view illustrating a heat transfer sheet according to at least one embodiment of the present disclosure.

As shown in FIGS. 12, 13, in the seventh embodiment, at least some of the heat transfer sheets 12 include a notch 12a. In the seventh embodiment, the thermal resistance of the heat transfer sheet 12 is adjusted by the notch 12a of the heat transfer sheet 12. In the seventh embodiment, the thermal resistance adjuster 14 is not provided.

As shown in FIG. 13, four heat transfer sheets 12 include the notch 12a, excepting one heat transfer sheet 12 that is the longest in the longitudinal direction in five heat transfer sheets 12 of the heat conduction device 1. At a portion of the heat transfer sheet 12 where the notch 12a is provided, the length in the width direction of the heat transfer sheet 12 is short. The longitudinal direction of the heat transfer sheet 12 is a direction in which the heat transfer sheet 12 connects the heat source portion 10 and the temperature control surface 11 (a left-right direction of FIG. 13). The width direction of the heat transfer sheet 12 is a direction perpendicular to the direction in which the heat transfer sheet 12 connects the heat source portion 10 and the temperature control surface 11 (an up-down direction of FIG. 13).

The thermal resistance R of the heat transfer sheet 12 having the notch 12a can be calculated by the following equation 1.

[Equation 1]

$$R = \frac{1}{\lambda \times d \times W} \times \left\{ L + \left( \frac{W}{W1} - 1 \right) \times L1 \right\} \quad (1)$$

Here, λ is the thermal conductivity of the heat transfer sheet 12, d is the thickness of the heat transfer sheet 12, W is the length of the heat transfer sheet 12 in the width direction, W1 is the length of the part of the heat transfer sheet 12 at which the notch 12a is provided, L is the length of the heat transfer sheet 12 in the longitudinal direction, and L1 is the length of the notch 12a in the longitudinal direction of the heat transfer sheet 12.

From equation 1, the thermal resistance R of the heat transfer sheet 12 can be adjusted by adjusting at least one of the length of the notch 12a in the longitudinal direction of the heat transfer sheet 12 and the length of the notch 12a in the width direction of the heat transfer sheet 12.

In the example shown in FIG. 13, the lengths of the notches 12a in the longitudinal direction of the heat transfer sheet 12 are uniformed, and the lengths of the notches in the width direction of the heat transfer sheet 12 are varied. Specifically, when the length of the heat transfer sheet 12 in the longitudinal direction is small, the length of the notch 12a in the width direction of the heat transfer sheet 12 is long. When the length of the heat transfer sheet 12 in the longitudinal direction is large, the length of the notch 12a in the width direction of the heat transfer sheet 12 is small, or the notch 12a is not provided. The thermal resistance can be uniformed among the heat transfer sheets 12 having different lengths.

In the seventh embodiment described above, the notches 12a are provided in the heat transfer sheets 12, and the thermal resistance is adjusted by adjusting the size of the notch 12a. Accordingly, the thermal resistance between the heat source portion 10 and the temperature control section 11a can be adjusted by varying the shape of the heat transfer sheets 12.

In the configuration of the seventh embodiment, the length of the notch 12a in the width direction of the heat transfer sheet 12 is varied between the heat transfer sheets 12. However, the length of the notch 12a in the longitudinal direction of the heat transfer sheet 12 may be varied.

In the seventh embodiment, the thermal resistance of the heat transfer sheet 12 is adjusted by providing the notch 12a in the heat transfer sheet 12, but a cut-off portion formed by cutting off a part of the heat transfer sheet 12 may be provided in addition to or instead of the notch 12a. The thermal resistance of the heat transfer sheet 12 can be adjusted by varying the length of the cut-off portion provided in the heat transfer sheet 12. Specifically, the thermal resistance can be increased by increasing the size of the cut-off portion, and the thermal resistance can be decreased by decreasing the size of the cut-off portion.

Eighth Embodiment

Next, an eighth embodiment of the present disclosure will be described. In the above-described embodiments, all of the heat transfer sheets 12 are connected to the heat source portion 10 directly or through the thermal resistance adjuster 14. In the eighth embodiment, some of the heat transfer sheets 12 are connected to the heat source portion 10.

Figure 14:
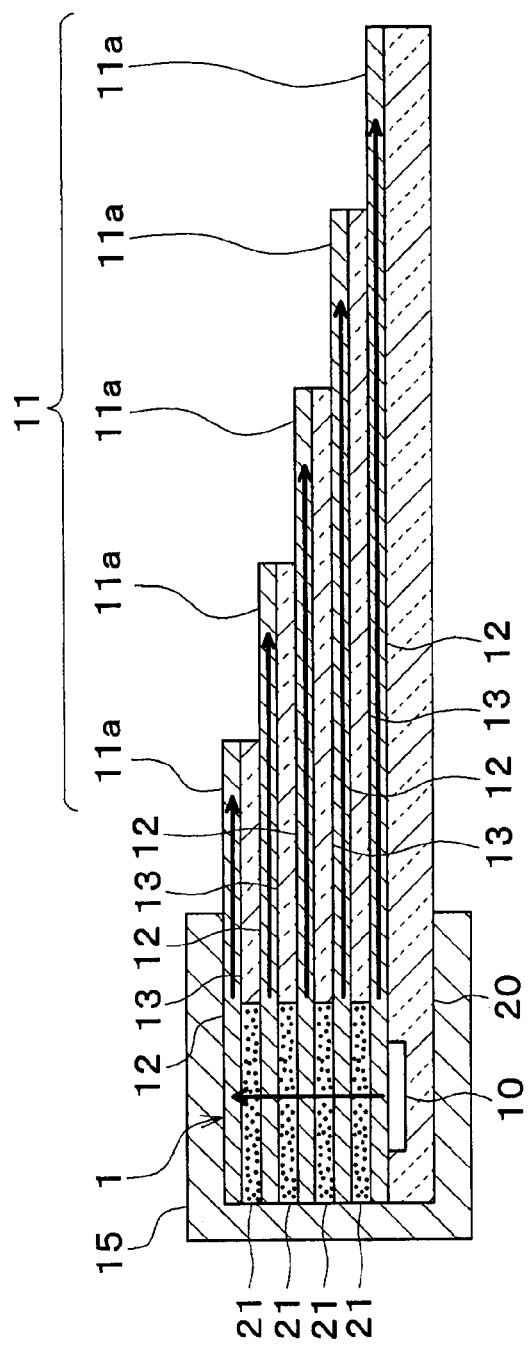
FIG. 14 is a cross-sectional diagram illustrating a heat conduction device according to at least one embodiment of the present disclosure.

As shown in FIG. 14, in the eighth embodiment, the heat source portion 10 is in contact with some of the heat transfer sheets 12 stacked with each other. In the example shown in FIG. 14, the heat source portion 10 is in contact with the outermost one of the heat transfer sheets 12. The heat source portion 10 is in contact with the heat transfer sheet 12 that is the longest in the heat transfer sheets 12. The heat source portion 10 and the heat transfer sheet 12 in contact with the heat source portion 10 are covered with an outer heat insulation sheet 20.

In the eighth embodiment, a peltier device that is a hot heat source is used as the heat source portion 10. Accordingly, hot heat is supplied to the temperature control surface 11 through the heat transfer sheet 12.

In the heat conduction device 1, the heat transfer sheets 12 and the heat insulation sheets 13 are alternately stacked with each other as in the above-described first embodiment. In the eighth embodiment, heat conductive stacking members 21 are provided between the heat transfer sheets 12 at a part overlapping the heat source portion 10 when viewed in the sheet stacking direction, instead of the heat insulation sheets 13. The heat is transferred in the sheet stacking direction between the heat transfer sheets 12 through the stacking members 21 at the part overlapping the heat source portion 10 in the sheet stacking direction.

The stacking member 21 of the eighth embodiment has adhesiveness. The heat transfer sheets 12 adjacent to each other can be bonded by using the adhesive stacking members 21, and the heat transfer sheets 12 can be joined in a stacking state. An adhesive tape such as Kapton (registered trademark of DuPont) film can be suitably used as the stacking member 21.

The thermal resistance of the stacking member 21 of the eighth embodiment in the sheet stacking direction can be adjusted. For example, the thermal resistance of the stacking members 21 can be adjusted by varying the shapes or the materials of the stacking members 21.

According to the above-described eighth embodiment, the heat conductive stacking members 21 are provided at the part corresponding to the heat source portion 10 in the configuration in which some of the heat transfer sheets 12 stacked with each other are in contact with the heat source portion 10. According to this, heat of the heat source portion 10 can be transferred in the sheet stacking direction, and the heat transfer sheets distant from the heat source portion 10.

Since the thermal resistance of the stacking members 21 can be adjusted in the eighth embodiment, the thermal resistance between the heat transfer sheets 12 in the sheet stacking direction can be adjusted. Accordingly, the thermal resistance between the heat source portion 10 and the temperature control sections 11a can be uniformed, and the temperature control sections 11a can be uniformly controlled.

The present disclosure is not limited to the embodiments described above, and various modifications can be made as follows within a range not departing from the spirit of the present disclosure.

In the above-described embodiments, the heat conduction device of the present disclosure is used in the temperature control seat for a vehicle. However, the heat conduction device can be used for different purposes. For example, the heat conduction device of the present disclosure may be used in a device that directly transfers heat to a human body such as a wheel heater. The heat conduction device may be used in a device that uses heat radiation or heat convection such as an underfloor radiator that radiates heat inside the passenger compartment from a part of a vehicle under the floor during a side-panel air-conditioning or parking.

In the above-described embodiments, the heat source portion 10 is the cooling water passage through which the heat medium flows. However, hot heat or cold heat may be directly generated in the heat source portion 10 by directly contacting a heat generating device or a cooling device, or by providing a heater or a peltier device in the heat source portion 10.

In the above-described embodiments, a part of the heat transfer sheet 12 constitutes the temperature control sections 11a. However, the heat transfer sheet 12 and the temperature control sections 11a may be provided as separated members.

In the above-described first embodiment, one thermal resistance adjuster 14 is provided between the heat source portion 10 and the heat transfer sheets 12. However, multiple thermal resistance adjusters 14 may be provided to correspond to multiple heat transfer sheets 12, and each thermal resistance adjusters 14 may be provided between the heat source portion 10 and each heat transfer sheets 12. In this case, the thermal resistance may be adjusted by each of the thermal resistance adjusters 14. The thermal resistance of the thermal resistance adjusters 14 can be adjusted by varying the shapes or the materials of the thermal resistance adjusters 14. The thermal resistance may be adjusted by making one thermal resistance adjuster 14 from multiple materials having different thermal conductivities.

Although the present disclosure has been described in accordance with the examples, it is understood that the present disclosure is not limited to the above examples or structures. To the contrary, the present disclosure is intended to cover various modification and equivalent arrangements. In addition, while the various elements are shown in various combinations and configurations, which are exemplary, other combinations and configurations, including more, less or only a single element, are also within the spirit and scope of the present disclosure.

Comparative Example

A heat conduction device is known, which takes heat of a human body or supplies heat to the human body by heat conduction by using, as a heat source (hot heat source or cold heat source), a peltier device or a metal pipe through which a heat medium whose temperature is controlled.

In such a heat conduction device, when a contact surface with the human body or clothes is formed directly on the surface of the heat source, the device tends to be large and rigid. For this reason, the heat conduction (heat transfer) member connected to the heat source may form a temperature control surface in contact with the human body. However, it may be difficult to adjust the temperature of a part distant from the heat source compared to a part close to the heat source, and uniform temperature adjustment over the entire temperature control surface may be difficult.

In a comparative example, to uniform the temperature of the entire temperature control surface, a pipe through which the heat medium flows is provided in the heat conduction device along the rim of the contact surface, and multiple heat conduction members are connected to the pipe. In the heat conduction device of, a metal plate such as an aluminum plate used as a heat spreader is inserted between the temperature control surface and the heat conduction member to control temperature of the temperature control surface more uniformly.

According to studies by the inventors of the present disclosure, in the heat conduction device of the comparative example, the thermal resistance may increase with the lengths of the heat conduction members from the heat source. Further, the heat transferred to a part of the heat conduction member close to the heat source may influence the heat transfer to a part distant from the heat source. Accordingly, temperature difference may occur between an end of the heat conduction member close to the heat source and another end, and it may be difficult to uniform the temperature of the entire temperature control surface. Further, when a metal plate is provided between the contact surface and the heat conduction member as a heat spreader, the metal plate is required to be thicker than a certain thickness to sufficiently spread heat in the contact surface, and accordingly the heat may not be sufficiently transferred from the heat source to the human body.

What is claimed is:

1. A heat conduction device comprising:
    a medium flow pipe through which a medium flows;
    a first heat transfer sheet and a second heat transfer sheet each of which is thermally conductive and is configured to exchange heat with the medium flowing through the medium flow pipe; and
    a heat insulator covering the first heat transfer sheet and the second heat transfer sheet, wherein
    the first heat transfer sheet extends from a first end close to the medium flow pipe to a second end away from the medium flow pipe,
    the second heat transfer sheet extends from a first end close to the medium flow pipe to a second end away from the medium flow pipe,
    the first heat transfer sheet and the second heat transfer sheet are stacked with each other such that the first end of the first heat transfer sheet and the first end of the second heat transfer sheet are aligned in a first direction,
    the first heat transfer sheet is longer than the second heat transfer sheet in a second direction perpendicular to the first direction and away from the medium flow pipe, and
    the second end of the first heat transfer sheet and the second end of the second heat transfer sheet are aligned in the second direction to define a temperature control surface.

2. The heat conduction device according to claim 1, wherein
    thermal resistance between the medium flow pipe and the second end of each of the first heat transfer sheet and the second heat transfer sheet is uniform.

3. The heat conduction device according to claim 2, further comprising:
    a thermal resistance adjuster, comprising a block of material, configured to adjust the thermal resistance between the medium flow pipe and the second end of each of the first heat transfer sheet and the second heat transfer sheet to be uniform.

4. The heat conduction device according to claim 3, wherein
the thermal resistance adjuster is made of metal.

5. The heat conduction device according to claim 3, wherein
the thermal resistance adjuster has corrosion resistance.

6. The heat conduction device according to claim 5, wherein
the thermal resistance adjuster is made of titanium.

7. The heat conduction device according to claim 3, wherein
the thermal resistance adjuster is made of a film or a tape.

8. The heat conduction device according to claim 3, wherein
the thermal resistance adjuster is located between the medium flow pipe and the first and second heat transfer sheets.

9. The heat conduction device according to claim 3, wherein
each of the first heat transfer sheet and the second heat transfer sheet is separated into a plurality of parts, and
the thermal resistance adjuster is located between the plurality of parts of the first heat transfer sheet and the second heat transfer sheet.

10. The heat conduction device according to claim 3, wherein
the thermal resistance adjuster is made of materials whose thermal conductivity is different from each other.

11. The heat conduction device according to claim 2, wherein
at least shapes or materials of the first heat transfer sheet and the second heat transfer sheet are different from each other, and thereby thermal resistance of the first heat transfer sheet and the second heat transfer sheet is different from each other.

12. The heat conduction device according to claim 11, wherein
the first heat transfer sheet or the second heat transfer sheet has a notch or a cut-off portion, and thereby the thermal resistance of the first heat transfer sheet is different from the thermal resistance of the second heat transfer sheet.

13. The heat conduction device according to claim 1, wherein
the second end of the first heat transfer sheet is smaller than the second end of the second heat transfer sheet.

14. The heat conduction device according to claim 1, wherein
the medium flow pipe is in contact with the first heat transfer sheet or the second heat transfer sheet,
a stacking member is provided between the first heat transfer sheet or the second heat transfer sheet, and
the stacking member is configured to adjust thermal resistance in the first direction.

15. The heat conduction device according to claim 14, wherein
the stacking member connects the first heat transfer sheet and the second heat transfer sheet.

16. The heat conduction device according to claim 1, wherein
thermal resistance of the first heat transfer sheet and the second heat transfer sheet in a direction in which the first heat transfer sheet and the second heat transfer sheet extend is higher than thermal resistance of the first heat transfer sheet and the second heat transfer sheet in another direction.

17. The heat conduction device according to claim 16, wherein
the thermal resistance of the first heat transfer sheet and the second heat transfer sheet in the direction in which the first heat transfer sheet and the second heat transfer sheet extend is more than 100 times higher than the thermal resistance of the first heat transfer sheet and the second heat transfer sheet in the another direction.

18. The heat conduction device according to claim 17, wherein
the first heat transfer sheet and the second heat transfer sheet are graphite sheets.

19. The heat conduction device according to claim 1, wherein
the first heat transfer sheet and the second heat transfer sheet and the heat insulator are stacked with each other.

20. The heat conduction device according to claim 1, wherein
the medium flowing through the medium flow pipe directly contacts the first heat transfer sheet and second heat transfer sheet.

21. The heat conduction device according to claim 1, wherein
the first end of the first heat transfer sheet is connected to the medium flow pipe, and
the first end of the second heat transfer sheet is connected to the medium flow pipe.

22. The heat conduction device according to claim 1, further comprising:
a thermal switch provided between the medium flow pipe and the first and second heat transfer sheets.

* * * * *